(12) United States Patent
Igami et al.

(10) Patent No.: US 9,297,815 B2
(45) Date of Patent: Mar. 29, 2016

(54) METHOD AND KIT FOR DETECTING CONDITION IN PATIENT WITH DISTURBANCE OF CONSCIOUSNESS

(75) Inventors: Ko Igami, Tokyo (JP); Tomoharu Okazaki, Kagoshima (JP); Koichi Shinmyozu, Kagoshima (JP); Tomoko Ono, Tokyo (JP); Fumio Furusaki, Tokyo (JP)

(73) Assignee: LSI MEDIENCE CORPORATION (JP)

( * ) Notice: Subject to any disclaimer, the term of this patent is extended or adjusted under 35 U.S.C. 154(b) by 1746 days.

(21) Appl. No.: 12/279,418

(22) PCT Filed: Feb. 15, 2007

(86) PCT No.: PCT/JP2007/052697
§ 371 (c)(1),
(2), (4) Date: Mar. 4, 2009

(87) PCT Pub. No.: WO2007/094394
PCT Pub. Date: Aug. 23, 2007

(65) Prior Publication Data
US 2009/0220990 A1    Sep. 3, 2009

(30) Foreign Application Priority Data

Feb. 16, 2006  (JP) ................................ 2006-039567

(51) Int. Cl.
*C12Q 1/37* (2006.01)
*G01N 33/86* (2006.01)
*C12Q 1/56* (2006.01)

(52) U.S. Cl.
CPC .... *G01N 33/86* (2013.01); *C12Q 1/56* (2013.01); *G01N 2800/2871* (2013.01); *G01N 2800/323* (2013.01)

(58) Field of Classification Search
None
See application file for complete search history.

(56) References Cited

U.S. PATENT DOCUMENTS

| | | | |
|---|---|---|---|
| 6,849,597 B2 * | 2/2005 | Murata et al. | 514/8.3 |
| 7,455,970 B2 * | 11/2008 | Jannes et al. | 435/6.16 |
| 7,575,872 B2 * | 8/2009 | Soejima et al. | 435/7.1 |
| 7,923,255 B2 * | 4/2011 | Ono | 436/69 |
| 8,088,624 B2 * | 1/2012 | Ono et al. | 436/69 |
| 2006/0251655 A1 | 11/2006 | Soejima et al. | |
| 2007/0275414 A1 | 11/2007 | Ono et al. | |
| 2008/0096221 A1 | 4/2008 | Ono | |

FOREIGN PATENT DOCUMENTS

| | | |
|---|---|---|
| WO | 03/016492 | 2/2003 |
| WO | 2004/029242 | 4/2004 |
| WO | 2005/062054 | 7/2005 |
| WO | 2006/049300 | 5/2006 |

OTHER PUBLICATIONS

Furlan et al., "Deficient activity of von Willebrand factor—cleaving protease in chronic relapsing thrombotic thrombocytopenic purpura." Blood 89(9): 3097-3103 (1997).*
Uemura et al. "Decreased activity of plasma ADAMTS13 may contribute to the development of liver disturbance and multiorgan failure in patients with alcoholic hepatitis." Alcoholism: Clinical and Experimental Research 29.s3 (2005): 264S-271S.*
Fujikawa et al., "Purification of human von Willebrand factor-cleaving protease and its identification as a new member of the metalloproteinase family", Blood, vol. 98(6), Sep. 15, 2001, 1662-1666.
Furlan et al., "Partial Purification and Characterization of a Protease From Human Plasma Cleaving von Willebrand Factor to Fragments Produced by In Vivo Proteolysis", Blood, vol. 87(10), May 15, 1996, 4223-4234.
Kokame et al., "Frets-VWF73, a first fluorogenic substrate for ADAMTS13 assay", British Journal of Haematology, 2005, vol. 129, 93-100.
Levy et al., "Mutations in a member of the ADAMTS gene family cause thrombotic thrombocytopenic purpura", Nature, vol. 413, Oct. 4, 2001, 488-494.
International Search Report for corresponding PCT/JP2007/052697 (WO 2007/094394).
Japan Intractable Diseases Information Center, Kessensei Kesshoban Genshosei Shihanbyo (TTP) [online], <http://www.nanbyou.or.jp/sikkan/026_i.htm> Aug. 17, 2005 uploaded, Japan Intractable Diseases Research Foundation, Ketsuekikei Shikkan Chosa Kenkyuhan (Ketsueki Gyoko Ijosho), retrieved on Apr. 6, 2007.
English Translation of the Written Opinion of the International Searching Authority for corresponding application PCT/JP2007/052697.
Supplementary European Search Report for corresponding application EP 07714227.1.
Furlan M., et al., "Acquired Deficiency of Von Willebrand Factor-Cleaving Protease in a Patient with Thrombotic Thrombocytopenic Purpura", Blood, American Society of Hematology, US, vol. 91(8), Apr. 15, 1998, 2839-2846.
Obert B., et al., "Estimation of the Von Willebrand Factor-Cleaving Protease in Plasma Using Monoclonal Antibodies to VWF", Thrombosis and Haemostasis, Stuttgard, DE., vol. 82(5), Nov. 1, 1999, 1382-1385.
Konetschny C., et al., "Development of a highly sensitive and specific enzyme-linked immunosorbent assay for the detection of ADAMTS-13 in human plasma", Blood, American Society of Hematology, US, vol. 102(11), Nov. 16, 2003, p. 89b. (Abstract Only).

* cited by examiner

*Primary Examiner* — Robert Yamasaki
(74) *Attorney, Agent, or Firm* — Heslin, Rothenberg, Farley & Mesiti P.C.

(57) ABSTRACT

A method for detecting a condition in a patient with disturbance of consciousness, by analyzing an amount and/or activity of a von Willebrand factor-cleaving protease, and a kit for detecting a condition in a patient with disturbance of consciousness, comprising an antibody or a fragment thereof which specifically binds to a von Willebrand factor-cleaving protease, or a von Willebrand factor or a fragment thereof, are disclosed. Examples of the detection of a condition include a detection of cerebrovascular disease, a detection of arteriosclerotic vascular disease, and a detection or prediction of severity.

7 Claims, 5 Drawing Sheets

METHOD AND KIT FOR DETECTING CONDITION IN PATIENT WITH DISTURBANCE OF CONSCIOUSNESS

CROSS REFERENCE TO RELATED APPLICATIONS

This application is a 371 filing of PCT Application No. PCT/JP2007/052697 filed Feb. 15, 2007 and published in Japanese as WO 2007/094394 on Aug. 23, 2007, which claims the priority of Japanese Application No. 2006-039567 filed Feb. 16, 2006. These disclosures and all other patents, published applications and other references cited herein are hereby incorporated by reference in their entirety.

TECHNICAL FIELD

The present invention relates to a method for detecting (determining or diagnosing) a condition in a patient with disturbance of consciousness (in particular, an unconscious patient such as a patient with stupor or coma). According to the present invention, the current extent of severity can be judged, or severity in future can be predicted, by analyzing (preferably, quantitatively measuring) the amount (concentration) and/or enzyme activity of a von Willebrand factor (hereinafter referred to as vWF)-cleaving protease contained in a biological sample (for example, blood) collected from a subject.

BACKGROUND ART

Stroke was, prior to 1980, the leading cause of death in this country, but has decreased by a factor of approximately 4 during the last 20 years, due to the progress in medical technology and development of emergency medical care. However, nowadays a rapid advance of an aging society tends to increase the number of stroke patients again. For the prevention thereof, daily health care is important. In addition, a patient's life can be prolonged by accurately determining the cause of disturbance of consciousness at an early stage of stupor or coma caused by stroke or the like, and selecting one or more appropriate options (a treatment, prognosis assessment, or the like).

Strokes are brain disorders caused by abnormalities in blood vessels (a paroxysmal disorder in which a cerebral blood vessel is ruptured or clogged due to a certain cause). An early and appropriate treatment is important, because stroke endangers the life or leaves sequelae such as paralysis or logopathy.

Strokes can be classified into two major categories: hemorrhage due to the rupture of a cerebral blood vessel, and ischemia due to the blockage of a cerebral blood vessel. Hemorrhagic strokes include subarachnoid hemorrhage and intracerebral hemorrhage, and ischemic strokes include cerebral infarction and transient ischemic attack.

Cerebral infarction, caused by the blockage of a cerebral artery by a thrombus, is the main type of strokes which are the third leading cause of death in Japan, and has a high mortality rate. Cerebral infarction is a state in which a cerebral artery is clogged due to a certain cause and, as a result, the blood flow to the subsequent tissues is disrupted or reduced. Approximately 20% of the total causes of death are cerebrovascular diseases, and cerebral infarction accounts for approximately 50% of these diseases. Cerebral infarctions can be classified into two major categories: cerebral embolism and cerebral thrombosis. Cerebral embolism is not directly caused by abnormalities in cerebral arteries, but is caused by an aggregate (such as blood, proteins, lipid, or the like) which is formed in the heart, due to a heart disease, accelerated to cerebral arteries, and blocks a cerebral artery. By contrast, cerebral thrombosis is developed due to arteriosclerosis of cerebral arteries itself. Cerebral thrombosis is more frequent than cerebral embolism.

As well as stroke, the causes of stupor or coma include, for example, the damage of the brain stem due to head injury or the like, alcoholism, an overdose of a drug such as a sedative, cardiac arrest, aneurysm, a severe pulmonary disease, inhalation of carbon monoxide, ictus epilepticus, hypothyroidism, hepatic failure, renal failure, hypoglycemia caused by diabetes, and the like. Therefore, many examinations are necessary to make a precise decision. For example, blood levels of sugar, sodium, alcohol, oxygen, carbon dioxide, and the like, counts of red blood cells and white blood cells, or sugar and toxic substances in urine, can be examined. Further, troponin or a heart-specific fatty acid-binding protein (H-FABP) may be measured to determine whether stupor or coma in a patient is caused by myocardial infarction, and an appropriate treatment may be selected. However, examples of a diagnostic method for arteriosclerosis as a cause of cerebral thrombosis include noninvasive examinations, such as fundoscopy, X-ray CT, MRI, a pulse wave velocity method, or blood flow monitoring using an ultrasonic wave, and invasive examinations, such as angiography, angioscopy, or intravascular ultrasound analysis. These methods are insufficient to monitor the extent of arteriosclerotic vascular disease or the progress of its symptoms.

It was suggested that a von Willebrand factor (hereinafter referred to as vWF)-cleaving protease [hereinafter referred to as ADAMTS13 (another name of the vWF-cleaving protease)] is involved in the onset of thrombotic thrombocytopenic purpura (TTP) which is very severe and has a high mortality rate; the vWF-cleaving protease was purified from plasma (nonpatent reference 1); and the gene was identified by cDNA cloning. It was actually revealed that genetic mutations of ADAMTS13 remarkably reduced the vWF-cleaving activity (nonpatent reference 2). An enzyme immunoassay utilizing monoclonal or polyclonal antibodies specific to ADAMTS13 was recently developed (patent reference 1), and a method for detecting causes of thrombosis involved in platelet aggregation, and the degree of thrombophilia in thrombosis was established. This method was used to find that the concentrations of ADAMTS13 contained in plasma samples collected from patients with thrombosis were remarkably lowered in comparison with those from healthy people.

For example, patent reference 2 discloses a method of detecting thrombosis or the degree of thrombophilia, characterized by measuring ADAMTS13, and discloses that examples of thrombosis include acute or chronic myeloid leukemia, acute promyelocytic leukemia, systemic lupus erythematosus, pulmonary embolism, cerebral infarction, veno-occlusive disease, acute lymphocytic leukemia, thrombotic microangiopathy, thrombotic thrombocytopenic purpura, hemolytic uremic syndrome, and deep vein thrombosis. Further, patent reference 3 discloses a method of detecting platelet thrombosis or organ failure in a patient suffering from disseminated intravascular coagulation (DIC) or systemic inflammatory response syndrome (SIRS), by analyzing ADAMTS13 and/or a cleaving factor thereof (such as elastase, plasmin, or thrombin).

As a conventional method for determining the ADAMTS13 activity, a method of the detection of large vWF multimers, using a combination of an SDS-agarose electrophoresis and autoradiography or Western blotting, was used (nonpatent reference 3). Further, FRETS-VWF73, which is prepared by introducing a fluorescent group and a quenching group into 73 residues of the A2 domain (i.e., the specific cleavage sites by ADAMTS13) of vWF, was developed and enabled the measurement of the ADAMTS13 activity to be conveniently performed (nonpatent reference 4).

[patent reference 1] WO 2004/029242
[patent reference 2] WO 2005/062054
[patent reference 3] WO 2006/049300
[non-patent reference 1] K. Fujikawa et al., Blood, (U.S.A.), 2001, vol. 98, p. 1662-6
[non-patent reference 2] G. G. Levy et al., Nature, (United Kingdom), 2001, vol. 413, p. 488-494
[non-patent reference 3] M. Furlan et al., Blood, (U.S.A.), 1996, vol. 87, p. 4223-4234
[non-patent reference 4] Kokame K et al., The British Journal of Haematology, (United Kingdom), 2005, vol. 129, p. 93-100

DISCLOSURE OF THE INVENTION

Problems to be Solved by the Invention

As described above, stupor or coma is caused by various origins, and it is important to determine a cause for each patient at an early stage. In particular, there are various examination methods to diagnose arteriosclerosis which is a cause of cerebral thrombosis in a patient with cerebrovascular disease, but these methods are insufficient to monitor the extent of arteriosclerotic vascular disease or the progress of its symptoms. Further, mechanisms and factors for the progress toward a condition accompanied by onset of disturbance of consciousness and/or multiple organ failure are not clarified, and thus, the prognoses of many patients were very poor. In patients with cerebrovascular disease, there is the possibility to protect against severely progressed conditions including multiple organ failure, by promptly finding a patient who will possibly fall into such severe symptoms and treating the patient with an appropriate therapy at an early stage.

The present inventors have conducted intensive studies, and have found that ADAMTS13 may be analyzed in a patient with stupor or coma (such as a patient with stroke) to determine a condition in the patient or predict the progress toward severe symptoms. More particularly, the inventors measured the concentration and/or activity of ADAMTS13 in plasma collected from a patient with cerebrovascular disease, and found that the concentration of ADAMTS13 was reduced in accordance with the extent of arteriosclerotic vascular disease. Further, in cases of severe hepatopathy, the inventors newly discovered that a patient with a remarkably decreased concentration and activity of ADAMTS13 fell into severe symptoms accompanied by disturbance of consciousness and multiple organ failure. As a result, the inventors found that the measurements thereof are useful in the prediction of severity and the monitoring of prognosis, and completed the present invention.

An object of the present invention is to provide a method and kit for detecting a condition in a patient with disturbance of consciousness.

Means for Solving the Problems

The object can be solved by the present invention, that is, a method for detecting a condition in a patient with disturbance of consciousness, characterized by analyzing the amount and/or activity of a von Willebrand factor-cleaving protease.

According to a preferred embodiment of the method, the detection of a condition is a detection of cerebrovascular disease, a detection of arteriosclerotic vascular disease, or a detection or prediction of severity.

According to another preferred embodiment of the method, the amount of a von Willebrand factor-cleaving protease is analyzed by an immunological method using an antibody or a fragment thereof which specifically binds to the von Willebrand factor-cleaving protease.

According to still another preferred embodiment of the method, the activity of a von Willebrand factor-cleaving protease is analyzed by using a von Willebrand factor or a fragment thereof.

Further, the present invention relates to a kit for detecting a condition in a patient with disturbance of consciousness, comprising an antibody or a fragment thereof which specifically binds to a von Willebrand factor-cleaving protease, or a von Willebrand factor or a fragment thereof.

According to a preferred embodiment of the kit, the detection of a condition is a detection of cerebrovascular disease, a detection of arteriosclerotic vascular disease, or a detection or prediction of severity.

The term "analysis" as used herein includes a detection to determine a presence or absence of a substance (for example, ADAMTS13) to be analyzed, and a measurement to quantitatively or semi-quantitatively determine the amount (concentration) or activity of a substance to be analyzed.

The term "to detect (determine) a condition(s)" as used herein includes, for example, to detect or predict a presence or absence, or the extent of cerebrovascular disease, to detect or predict the severity of various symptoms [for example, cerebrovascular disease and/or other complications (such as disturbance of consciousness, multiple organ failure, and hepatopathy)], to predict the onset (i.e., to evaluate the risk of onset) of various symptoms [for example, cerebrovascular disease and/or other complications (such as disturbance of consciousness, multiple organ failure, and hepatopathy)], to perform a prognosis of various symptoms [for example, cerebrovascular disease and/or other complications (such as disturbance of consciousness, multiple organ failure, and hepatopathy)], a monitoring, a decision of a treatment, and the like.

Effects of the Invention

According to the present invention, the current severity can be judged, or severity in future can be predicted, in a patient with disturbance of consciousness.

For example, in a patient with disturbance of consciousness (for example, a patient with cerebrovascular disease), a patient who will possibly fall into severe symptoms accompanied by onset of disturbance of consciousness and/or multiple organ failure can be promptly found, and thus, the clinical value of the present invention is considered extremely high. According to the present invention, disturbance of consciousness and/or multiple organ failure can be detected conveniently, rapidly, and specifically. Further, from Examples described below, "a remarkable decrease in ADAMTS13" may be suggested as a new cause of onset of multiple organ failure or disturbance of consciousness, and it is considered that the progress of symptoms may be prevented by a treatment to increase or maintain ADAMTS13 [for example, a transfusion of fresh frozen plasma (FFP), a plasma exchange, or the like], which has not previously been used in treating such patients. This shows that a monitoring of ADAMTS13 can be directly used in evaluating the effects of the above treatment for patients with cerebral infarction.

BEST MODE FOR CARRYING OUT THE INVENTION

Figure 1:
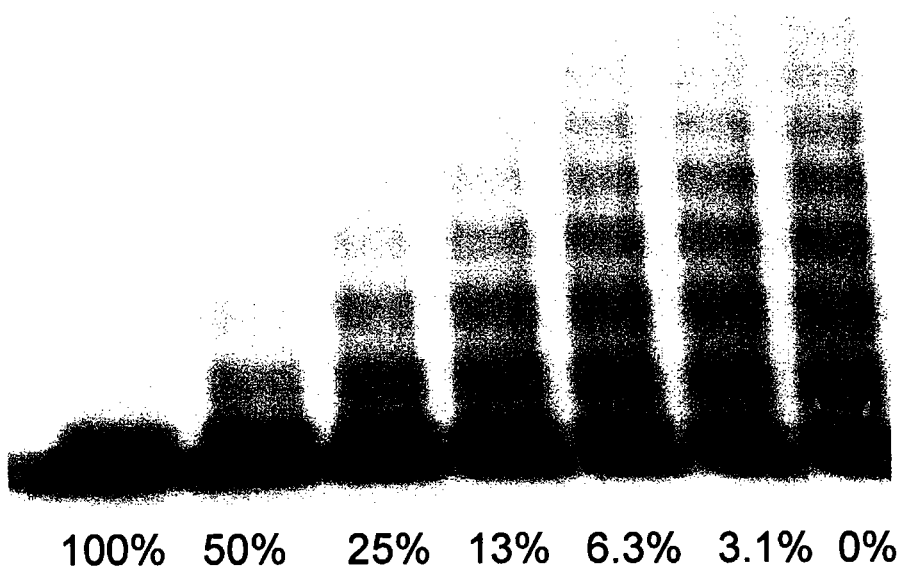
FIG. 1 is a photograph, instead of a drawing, showing the result of an SDS-agarose gel electrophoresis of vWFs treated with a normal human pooled serum and a dilution series thereof, which contain ADAMTS13.

[1] Detection Method of the Present Invention

In the method of the present invention, a condition in a patient with disturbance of consciousness can be detected, by analyzing (preferably measuring or quantitatively determining) at least one of the amount (concentration) and enzyme activity of ADAMTS13, and comparing the measured value(s) with one(s) of healthy people, or by measuring or quantitatively determining the amount (concentration) and enzyme activity of ADAMTS13 sequentially.

The method of the present invention may comprise
(1) the step of analyzing the amount (concentration) or enzyme activity of ADAMTS13 in a sample to be analyzed, and
(2) the step of comparing the obtained value(s) with one(s) of one or more healthy people.

Alternatively, the method of the present invention may comprise
(1) the step of sequentially analyzing the amount (concentration) or enzyme activity of ADAMTS13 in a sample to be analyzed, and
(2) the step of characterizing a tendency of the obtained time-course.

The term "von Willebrand factor-cleaving protease (vWF-cleaving protease)" as used herein means a metalloprotease, sometimes referred to as ADAMTS13, which specifically cleaves the von Willebrand factor (VWF) at the bond between tyrosine (842) and methionine (843) contained in an A2 domain thereof.

In the method of the present invention, a decrease in the amount (concentration) and/or enzyme activity of ADAMTS13 can be used as an index, in comparison with those of healthy people. Further, in the method of the present invention, a time-course of the amount (concentration) and/or enzyme activity of ADAMTS13 may be measured to use a decreasing tendency obtained from the time-course as an index. For example, in a patient who advanced toward a condition accompanied by onset of disturbance of consciousness and/or multiple organ failure, as shown in Examples described below, the concentration and enzyme activity of ADAMTS13 contained in a body fluid had been remarkably decreased, even before the progress to the above condition, in comparison with those of healthy people.

In the method of the present invention, when the measured or quantitatively-determined concentration and/or enzyme activity of ADAMTS13 are lower than normal ranges of healthy people (for example, lower than thresholds), or when a time-course of the concentration and/or enzyme activity of ADAMTS13 is measured or quantitatively-determined, and the time-course shows a decreasing tendency, it may be judged that a subject suffers from cerebrovascular disease (or the level of cerebrovascular disease is high), or it may be predicted that the risk of onset of cerebrovascular disease is high. Further, it may be judged that the severity of various symptoms [for example, cerebrovascular disease and/or other complications (such as disturbance of consciousness, multiple organ failure, and hepatopathy)] is high, it may be predicted that the risk of onset of various symptoms [for example, cerebrovascular disease and/or other complications (such as disturbance of consciousness, multiple organ failure, and hepatopathy)] is high, and it may be predicted that the prognosis of various symptoms [for example, cerebrovascular disease and/or other complications (such as disturbance of consciousness, multiple organ failure, and hepatopathy)] is poor.

By contrast, when the concentration and/or enzyme activity of ADAMTS13 fall within normal ranges, or when a time-course of the concentration and/or enzyme activity of ADAMTS13 is measured or quantitatively-determined, and the time-course shows an increasing tendency, it may be judged that a subject does not suffer from cerebrovascular disease (or the level of cerebrovascular disease is low), or it may be predicted that the risk of onset of cerebrovascular disease is low. Further, it may be judged that the severity of various symptoms [for example, cerebrovascular disease and/or other complications (such as disturbance of consciousness, multiple organ failure, and hepatopathy)] is low, it may be predicted that the risk of onset of various symptoms [for example, cerebrovascular disease and/or other complications (such as disturbance of consciousness, multiple organ failure, and hepatopathy)] is low, and it may be predicted that the prognosis of various symptoms [for example, cerebrovascular disease and/or other complications (such as disturbance of consciousness, multiple organ failure, and hepatopathy)] is good.

Examples of a subject to whom the method of the present invention may be applied (i.e., a person to be diagnosed) include a patient with disturbance of consciousness, in particular, an unconscious patient such as a patient with stupor or coma, and a patient with cerebrovascular disease (a patient with stroke) is preferred.

Examples of cerebrovascular disease include transient ischemic attack, atherothrombotic cerebral infarction, cardioembolic brain infarction, lacunar brain infarction, cerebral hemorrhage, subarachnoid hemorrhage, intracranial hemorrhage, cerebrovascular dementia, and hypertensive encephalopathy. Examples of hepatopathy include acute viral hepatitis, chronic viral hepatitis, autoimmune hepatitis, alcoholic hepatopathy, cirrhosis, primary biliary cirrhosis, hepatocellular carcinoma, and drug-induced hepatopathy. Arteriosclerotic vascular disease is a condition which mainly occurs in the aorta, coronary artery, cerebral artery, or carotid artery, and is a main factor of myocardial infarction, cerebral infarction, or the like. It is considered that the formation of atherosclerotic plaques begins due to the damage of vascular endothelial cells; aggregation and adhesion of platelets at the damaged site, migration of vascular smooth muscle cells to tunica intima and proliferation of the smooth muscle cells, migration of macrophages to aggregated platelets, formation of the atherosclerotic plaques (atheromas) due to transformation of smooth muscle cells or macrophages into foam cells, and induration due to collagen adsorption occur; and the atherosclerotic plaques are completed. The atherosclerotic plaques are structurally fragile, and ruptured by a hemodynamic force as a trigger, to rapidly form a thrombus by reactions of tissue factors and blood coagulation factors. Risk factors of arteriosclerotic vascular disease include high blood pressure, hyperlipemia, tobacco smoking, obesity, gout, stress, a sedentary lifestyle, type A behavioral pattern, and low serum concentrations of HDL cholesterol, and the like. Due to the increase in such lifestyle related diseases, in cerebrovascular diseases, atherothrombotic cerebral infarction and cardioembolic brain infarction are on the increase. In cerebrovascular diseases, these diseases due to arteriosclerotic vascular disease are ischemic cerebral infarction. Examples thereof include atherothrombotic cerebral infarction caused by artery stenosis or occlusion due to atheroma formation in the cerevoical part of the internal carotid artery or the horizontal part of the middle cerebral artery; artery embolism due to arteriosclerosis in a relatively thin blood vessel such as the common carotid artery at the neck; cardioembolic brain infarction due to the sudden occlusion of the internal carotid artery or cerebral artery by a migration of a fibrin thrombus (which is formed in the cardiac cavity due to cardiac dysrhythmia or the like caused by coronary disease) and accompanied by rapid cerebral circulation disorder; lacunar brain infarction in which the main cause is arteriocapillary sclerosis in penetrating arteries and high blood pressure is considered a risk factor.

In the method of the present invention, the detection and/or prediction may be carried out, by collecting samples from one or more healthy people and a subject, measuring the concentration and/or enzyme activity of ADAMTS13 contained in the samples, and comparing the measured values. In general, it is preferable that samples collected from healthy people are used to determine normal ranges of the concentration and/or enzyme activity of ADAMTS13, or thresholds thereof for judgment in advance. When the normal ranges or the thresholds for judgment are determined in advance, the detection and/or prediction in a subject can be carried out, only by analyzing ADAMTS13 with respect to the subject to be assessed. The normal ranges or the thresholds for judgment are considered to depend on various conditions, such as an underlying disease, sex, or age. However, those skilled in the art can easily determine the normal ranges or the thresholds for judgment, by selecting an appropriate statistical population corresponding to the subject(s) and statistically processing data obtained from that population.

For example, in the population shown in Examples described below, values regarded as abnormal were 50% or less and 40% or less, with respect to the concentration of ADAMTS13 and the enzyme activity of ADAMTS13, respectively.

In the method of the present invention, a method of analyzing the concentration or enzyme activity of ADAMTS13 is not limited, so long as the concentration or enzyme activity of ADAMTS13 may be quantitatively or semi-quantitatively determined, or a presence or absence of ADAMTS13 may be judged, by the analyzing method.

Examples of the method of analyzing the concentration of ADAMTS13 include an immunological method using an anti-ADAMTS13 antibody or a fragment thereof (such as an enzyme-linked immunosorbent assay, a latex agglutination immunoassay, a chemoluminescence immunoassay, a fluorescent antibody method, a radioimmunoassay, immunoprecipitation, immunohistochemical staining, or Western blotting), a biochemical method (such as an enzymological method), or a molecular biological method for measuring an mRNA.

When an immunological method is used in analyzing ADAMTS13, an anti-ADAMTS13 antibody or a fragment thereof may be prepared in accordance with a known method, such as a method described in WO 2004/029242. Each immunoassay may be carried out in accordance with, for example, WO 2004/029242.

As a method of measuring the concentration of ADAMTS13, an immunological method is preferable from the viewpoint of sensitivity and convenience. The immunological method means a method of analyzing ADAMTS13 by an ELISA method, a latex method, immunochromatography, or the like, using an antibody against ADAMTS13. Examples of the immunological method include a competition method using a labeled ADAMTS13, a sandwich method using a labeled antibody, a latex bead method in which an agglutination of beads coated with an antibody is observed, and a method using an antibody conjugated to a colored particle such as gold colloid. Any method using the antibody against ADAMTS13 is included in preferred embodiments of the present invention. The antibody may be monoclonal or polyclonal. An antibody fragment, such as FAb, FAb', $F(Ab')_2$, or Fv, may be used.

Examples of the method of analyzing the enzyme activity of ADAMTS13 include a biochemical method using vWF of a fragment thereof [for example, a method of the detection of large vWF multimers, using a combination of an SDS-agarose electrophoresis and autoradiography or Western blotting (nonpatent reference 3), or a method of detecting a vWF cleaving activity, using a substrate prepared by introducing a fluorescent group [2-(N-methylamino)benzoyl, Nma] and a quenching group (2,4-dinitrophenyl, Dnp) into a synthetic peptide corresponding to 73 residues of ASP1596-Arg1668 located in the A2 domain of vWF (nonpatent reference 4)], and an immunological method using vWF or a fragment thereof, and an antibody or a fragment thereof specific to the cleavage site of vWF by ADAMTS13.

Further, as the method of analyzing the enzyme activity of ADAMTS13, a method using a synthetic substrate or an immunoassay may be used. These methods may be carried out, for example, in accordance with a method described in the specification of Japanese Patent Application No. 2005-148793, that is, an analyzing method comprising the steps of (1) in a liquid, bringing a sample possibly containing ADAMTS13 into contact with an immobilized substrate prepared by binding vWF or a fragment thereof to an insoluble carrier, (2) separating the liquid from the insoluble carrier, and (3) analyzing the vWF or the fragment thereof which remains in the insoluble carrier, and/or a vWF fragment (i.e., substrate fragment) which is released from the insoluble carrier and is contained in the liquid. Such analyzing methods include an embodiment in which the vWF or the fragment thereof bound on the insoluble carrier is labeled with a labeling substance, at the side of the substrate fragment released from the insoluble carrier by the cleavage with ADAMTS13. Further, an antibody or a fragment thereof, or aptamer or the like, which specifically binds to a neoantigen newly generated by cleaving vWF with ADAMTS13 (i.e., a partial sequence containing the amino acid located at the section), may be labeled with a labeling substance, and used in the analysis step to analyze the enzyme activity. Examples of the labeling substance include a fluorescent substance, a luminescent substance, a color developing substance, and an enzyme. Examples of the insoluble carrier include latex particles formed from various plastics (such as polypropylene, polystyrene, polycarbonate, polyamide, and polytetrafluoroethylene), glass particles, magnetic particles, and a microtiter well.

A preferred sample to be assayed by the method of the present invention is, for example, blood such as plasma or a serum. Examples of samples other than blood include various body fluids, such as cell or tissue fluids, lymph, a thymic fluid, an ascites fluid, an amniotic fluid, gastric juices, urine, pancreatic juices, spinal fluid, and saliva.

[2] Detection Kit of the Present Invention

The detection kit of the present invention may be used to carry out the method of the present invention. According to subjects to be analyzed to detect the above-mentioned conditions, the detection kit of the present invention includes a detection kit of analyzing the concentration of ADAMTS13 (hereinafter referred to as a concentration-analysis-type kit), and a detection kit of analyzing the enzyme activity of ADAMTS13 (hereinafter referred to as an activity-analysis-type kit).

The concentration-analysis-type kit of the present invention comprises at least an anti-ADAMTS13 antibody or a fragment thereof, and preferably comprises two or more different types of anti-ADAMTS13 antibodies. The anti-ADAMTS13 antibodies may be monoclonal or polyclonal. When two or more different types of anti-ADAMTS13 antibodies are contained in the kit, either of the antibodies (second antibody) may be labeled (i.e., labeling), or a labeled antibody specific to the second antibody may be added to the kit, instead of the labeling.

The activity-analysis-type kit of the present invention comprises at least vWF or a fragment thereof. Further, vWF or a fragment thereof contained in the kit may be labeled. Furthermore, instead of the labeling, an antibody or a fragment thereof which specifically binds to a neoantigen newly generated by cleaving vWF with ADAMTS13 (i.e., a partial sequence containing the amino acid located at the section) may be added to the kit.

EXAMPLES

The present invention will now be further illustrated by, but is by no means limited to, the following Examples.

Example 1

Measurement of ADAMTS13 Activity by SDS-Agarose Gel Electrophoresis

A normal human pooled serum and a dilution series thereof, which contained ADAMTS13, were mixed with an equal volume of a Tris buffer (pH7.4; containing 1.5 mol/L urea and 0.1 mol/L barium chloride), and were supplemented with 4-[2-aminoethyl]-benzenesulfonyl fluoride, hydrochloride; Pefabloc (Roche) in a final concentration of 2.4 mmol/L. These sample solutions were mixed with a Tris buffer (pH7.4, 1.5 mol/L urea) containing 3 µg/mL of vWF (purified from human plasma in accordance with the method described in nonpatent reference 3) at a volume ratio of 1:5, and incubated at 37° C. overnight to cleave the recombinant vWF with ADAMTS13 contained in the sample solutions. The cleavage reaction was terminated by adding EDTA thereto in a final concentration of 40 mmol/L. These treated samples were subjected to an SDS-agarose gel electrophoresis (1.4% agarose gel), and separated vWF bands were transferred to a polyvinylidene difluoride (PVDF) membrane by Western blotting. The membrane was blocked with a commercially available blocking agent (BlockAce; Dainippon Pharmaceutical) at room temperature, and washed with a Tris buffer (pH7.4). The membrane was reacted with an HRP (horseradish peroxidase)-labeled anti-vWF antibody (DAKO) [1:1000 diluted with Tris buffer (pH7.4)/10% BlockAce] at room temperature for an hour, and washed with a Tris buffer (pH7.4) three times. The vWF bands were visualized by using a commercially available developing kit (Immunostain HRP-1000; Konica).

The result of the electrophoresis is shown in FIG. 1. In FIG. 1, the value (unit=%) shown in each lane is a content of the normal human pooled serum contained in the pooled serum and the diluted series thereof, when the normal human pooled serum is regarded as 100%. ADAMTS13 contained in each sample cleaved vWF, and vWF bands having a different length according to their multimer size were detected.

Figure 2:
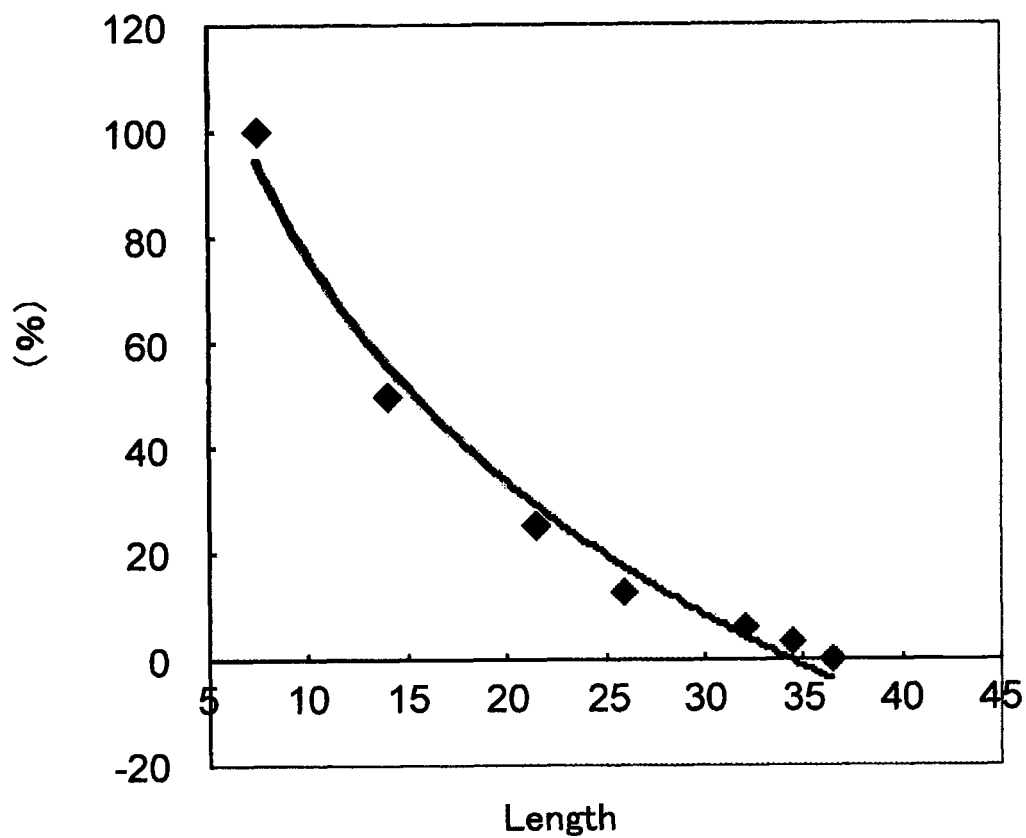
FIG. 2 is a standard curve prepared from the electrophoretic pattern shown in FIG. 1.

A standard curve in which the X-axis is the length (unit=mm) of each vWF band, and the Y-axis is the content of the pooled serum was prepared and is shown in FIG. 2.

Example 2

Measurement of Amount of ADAMTS13 Antigen in Cases of Cerebrovascular Disease

Plasma samples collected from patients with atherothrombotic cerebral infarction and patients with lacunar brain infarction were tested to measure the amount of an ADAMTS13 antigen. The amount of the ADAMTS13 antigen was measured using a commercially available kit (vWF cleaving enzyme ELISA kit; Mitsubishi Kagaku Iatron).

Figure 3:
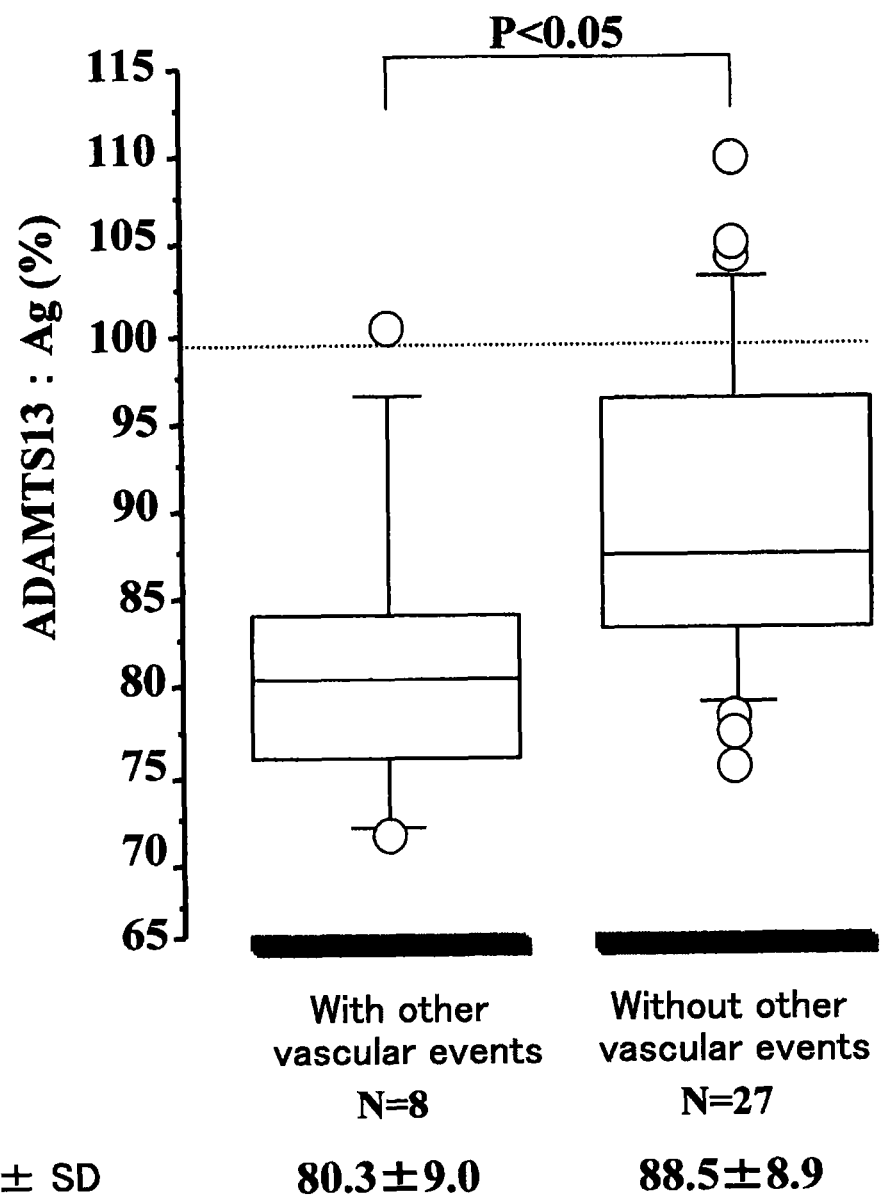
FIG. 3 is a graph showing the results of a statistical analysis of the amounts of an ADAMTS13 antigen in cases of atherothrombotic cerebral infarction.
Figure 4:
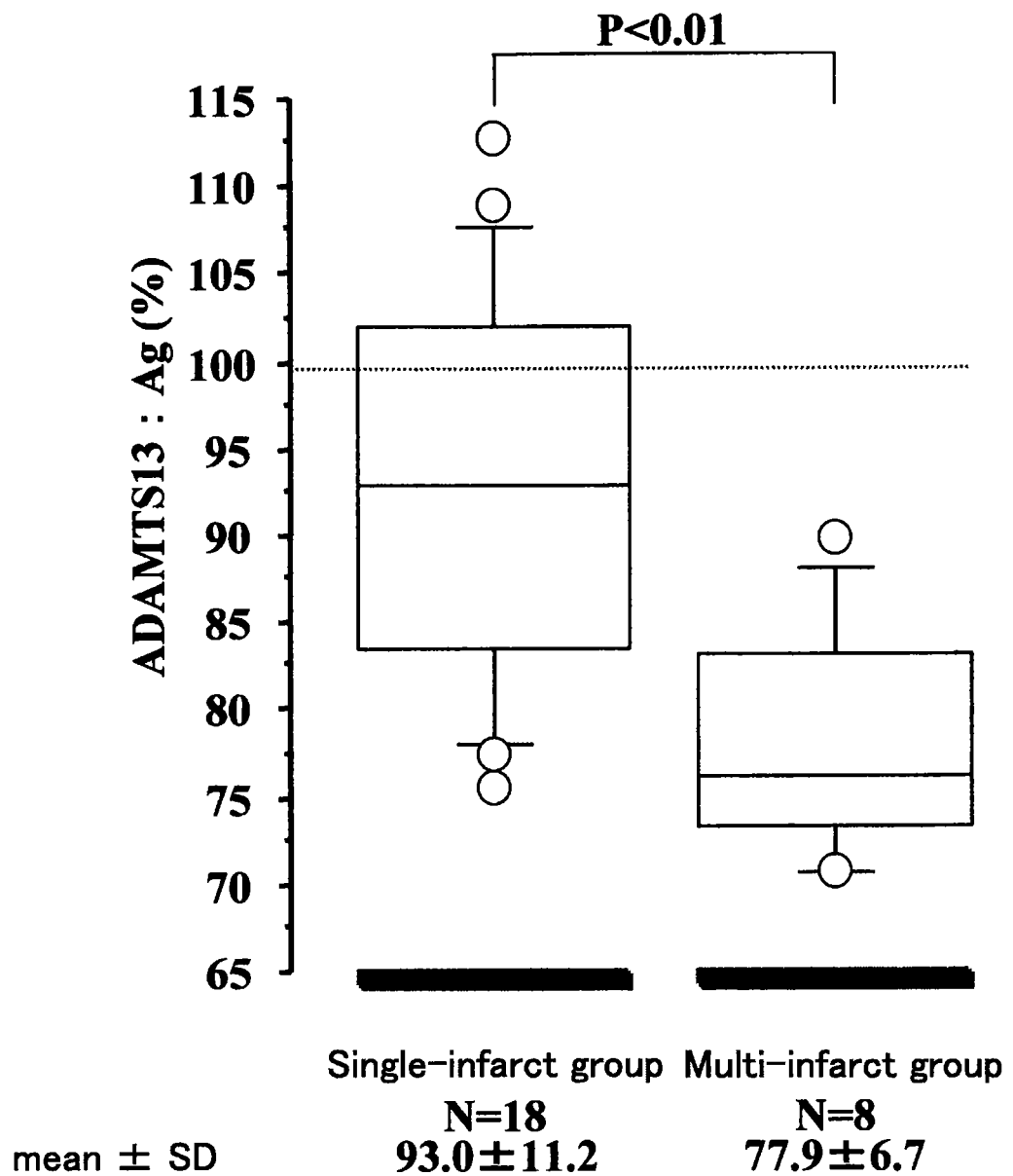
FIG. 4 is a graph showing the results of a statistical analysis of the amounts of an ADAMTS13 antigen in cases of lacunar brain infarction.

The results with respect to the cases of atherothrombotic cerebral infarction and lacunar brain infarction are shown in FIGS. 3 and 4, respectively. In FIGS. 3 and 4, the Y-axis is the amount of the ADAMTS13 antigen (unit=%), when the amount of the ADAMTS13 antigen contained in the normal human pooled serum is regarded as 100%. "P<0.05" shown in FIG. 3 means that there is a significant difference: level of significance is less than 5%. "P<0.01" shown in FIG. 4 means that there is a significant difference: level of significance is less than 1%.

In the cases of atherothrombotic cerebral infarction (FIG. 3), the amount of the ADAMTS13 antigen is compared in the presence and absence of complication of vascular events [for example, old myocardial infarction (OMI) and/or arteriosclerosis obliterans (ASO)] at other regions (i.e., regions other than the brain). The amount of the ADAMTS13 antigen in the group with the complication of vascular events at other regions was significantly lowered in comparison with that in the group without the complication.

In the cases of lacunar brain infarction (FIG. 4), the patients were classified into a single-infarct group and a multi-infract group according to an MRI analysis, and the amount of the ADAMTS13 antigen is compared between the groups. The amount of the ADAMTS13 antigen in the multi-infract group was significantly lowered in comparison with that in the single-infarct group.

The results shown in FIGS. 3 and 4 suggest that when the blood concentration of ADAMTS13 is low in a patient with cerebrovascular disease, arteriosclerotic vascular disease is progressing, and this indicates that ADAMTS13 is useful as a marker reflecting the extent of cerebrovascular disease. For example, atherothrombotic cerebral infarction is caused by artery stenosis or occlusion due to atheroma formation in the cervical part of the internal carotid artery or the horizontal part of the middle cerebral artery. Further, old myocardial infarction and arteriosclerosis obliterans are regarded as arteriosclerotic vascular disease. Furthermore, lacunar brain infarction is mainly caused by arteriocapillary sclerosis in penetrating arteries. In a patient with multiple lacunar infarct, arteriosclerosis is often observed in arteries other than cerebral arteries, and it is considered that arteriosclerotic vascular disease is progressing in comparison with single-infarct.

Example 3

Clinical Observations and ADAMTS13 Values in Patients Who Advanced Toward a Condition Accompanied by Onset of Disturbance of Consciousness and/or Multiple Organ Failure In 133 cases of cerebrovascular disease from the subacute phase to the chronic phase, including 50 cases of atherothrombotic cerebral infarction, 22 cases of cardioembolic brain infarction, 34 cases of lacunar brain infarction, 19 cases of cerebral hemorrhage, and 8 cases of subarachnoid hemorrhage, the enzyme activity of ADAMTS13 was measured by the SDS-agarose gel electrophoresis described in Example 1, and the amount of the ADAMTS13 antigen was measured by the commercially available kit (vWF cleaving enzyme ELISA kit; Mitsubishi Kagaku Iatron) described in Example 2. In 6 cases of these cases, the ADAMTS13 activity was lower than 30%. All of the 6 cases were cerebral infarction [3 cases of cardioembolic brain infarction (CEBI) and 3 cases of lacunar brain infarction (LBI)], and were accompanied by severe hepatopathy (1 case of cholangiocarcinoma, 1 case of alcoholic hepatitis, and 4 cases of chronic hepatitis C) and disturbance of consciousness. The clinical observations and ADAMTS13 values in the 6 cases are shown in Table 1.

sciousness and multiple organ dysfunction syndrome (MODS) appeared on Sep. 10, 2004, the conditions gradually became worse, and she died on Sep. 28, 2004.

It is strongly suggested by the above results that a remarkably decreased ADAMTS13 in a patient with severe hepatopathy promotes disturbance of consciousness and MODS. That is, it is considered that the "remarkable decrease in ADAMTS13" by itself plays an important role for the progress toward a condition accompanied by onset of disturbance of consciousness and/or multiple organ dysfunction. In addition, in case no. 6 among the above 6 cases [that is, the case where the ADAMTS13 activity was low (21%), but the activity was maintained and was not decreased from the level], the patient did not advance to MODS, and avoided a poor prognosis. This result does not only suggest a possibility that the "remarkable decrease in ADAMTS13" is a cause for the progress of severe conditions, but also indicates a novel effectiveness in an ADAMTS13 substitution therapy which has not been used in the past. The progress toward MODS can be promptly predicted and a treatment can be determined at an early stage, by monitoring the amount of the ADAMTS13 antigen and the enzyme activity thereof and detecting the extent of the decrease, and it is concluded that this will become a diagnosis that can save the lives of patients.

INDUSTRIAL APPLICABILITY

The present invention can be applied to a use for detecting conditions in patients with disturbance of consciousness.

Although the present invention has been described with reference to specific embodiments, various changes and modifications obvious to those skilled in the art are possible without departing from the scope of the appended claims.

TABLE 1

| Cases | | | | ADAMTS13 on admission | | Complications | ADAMTS13 on discharge |
| --- | --- | --- | --- | --- | --- | --- | --- |
| No. | Age | Sex | Type | Antigen(%) | Activity(%) | on admission | Activity(%) |
| 1 | 81 | Female | CEBI | 30.6 | 14.7 | Cholangiocarcinoma Metastatic hepatoma Cholangitis | 0.0 |
| 2 | 61 | Male | CEBI | 31.1 | 13.9 | Alcoholic hepatitis Cirrhosis Pneumonia | 0.0 |
| 3 | 69 | Male | CEBI | 33.2 | 14.2 | Hepatitis C Cirrhosis | 0.0 |
| 4 | 76 | Male | LBI | 39.2 | 20.8 | Hepatitis C Pulmonary carcinoma Cirrhosis Pneumonia | 3.4 |
| 5 | 84 | Male | LBI | 37.8 | 18.8 | Hepatitis C Pneumonia | 0.0 |
| 6 | 70 | Male | LBI | 38.4 | 21.2 | Hepatitis C Cholecystitis | 39.4 |

In 5 cases (case nos. 1 to 5) of the above 6 cases as shown in Table 1, the patients exhibited a further decrease in activity of ADAMTS13 in hospital, advanced to multiple organ dysfunction syndrome (MODS), and later died. By contrast, the patient of case no. 6 did not advance to MODS, avoided a poor prognosis, and is still alive.

Figure 5:
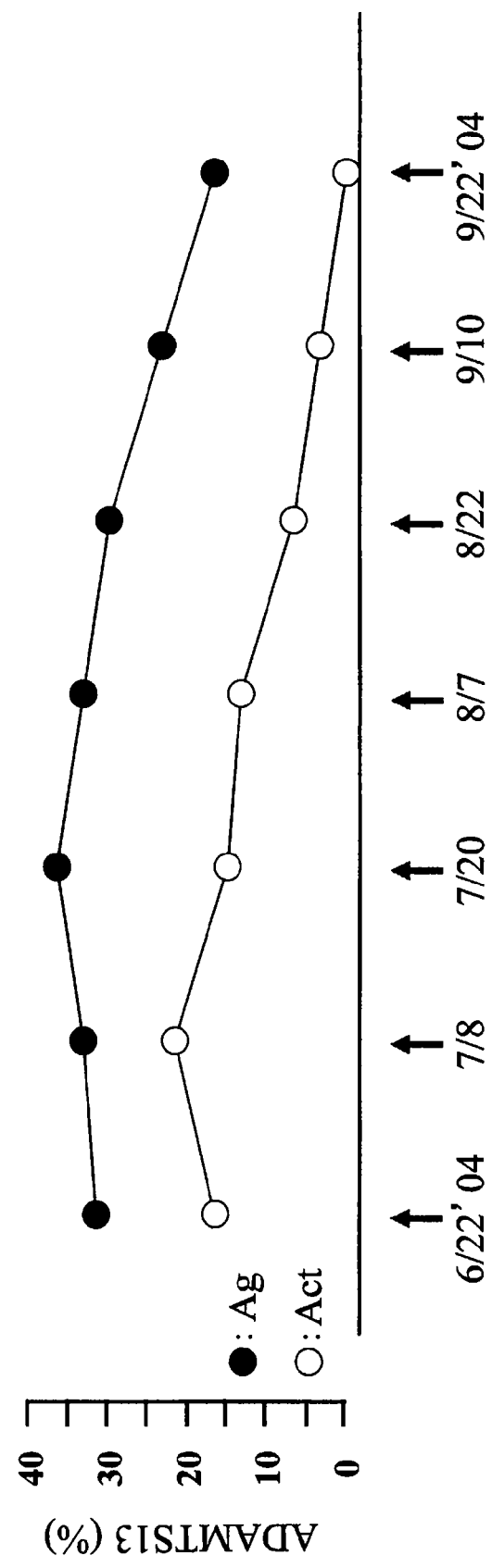
FIG. 5 is a graph showing the clinical progress of case no. 1 in Example 3.

The clinical progress in case no. 1 is shown in FIG. 5. In FIG. 5, the abbreviations "Ag" and "ACT" mean the amount of the ADAMTS13 antigen and the enzyme activity of ADAMTS13, respectively. The patient of case no. 1 was admitted to hospital (onset of cholangiocarcinoma, multiple liver metastases, and recurrent cholangitis as underlying diseases on admission) on Jun. 22, 2004, disturbance of con-

The invention claimed is:

1. A method for identifying and treating a patient among patients with cerebrovascular disease-associated infarction with stupor or coma accompanied by severe hepatopathy who is likely to advance to multiple organ dysfunction syndrome (MODS), the method comprising:

determining an activity of a von Willebrand factor-cleaving protease in a blood sample from the patient, wherein an activity of said von Willebrand factor-cleaving protease in said sample prior to treatment that is equal to or lower than 40% compared to the activity in healthy individuals identifies the patient as likely to advance to MODS; and administering a treatment to said patient to increase or maintain von Willebrand factor-cleaving protease activity.

2. The method according to claim 1, wherein the cerebrovascular disease is arteriosclerotic cerebrovascular disease selected from the group consisting of atherothrombotic cerebral infarction, cardioembolic brain infarction and lacunar brain infarction.

3. The method of claim 1, wherein the activity of a von Willebrand factor-cleaving protease is analyzed using a von Willebrand factor or a fragment thereof.

4. The method according to claim 3, wherein the activity of a von Willebrand factor-cleaving protease is analyzed using a von Willebrand factor or a fragment thereof having an 842 tyrosine-843 methionine bond which is a specific cleavage site for the von Willebrand factor-cleaving protease.

5. The method of claim 1, wherein the treatment to increase or maintain von Willebrand factor-cleaving protease activity comprises:
   transfusing fresh frozen plasma to the patient.

6. The method of claim 1, wherein the treatment to increase or maintain von Willebrand factor-cleaving protease activity comprises:
   performing a plasma exchange on the patient.

7. The method of claim 1, wherein the treatment to increase or maintain von Willebrand factor-cleaving protease activity comprises:
   performing a von Willebrand factor-cleaving protease substitution therapy on the patient.

* * * * *